United States Patent [19]

Wolf et al.

[11] 4,323,681
[45] Apr. 6, 1982

[54] 4-AMINO-2-SUBSTITUTED-5-PYRIMIDINECARBOXAMIDOXIMES AND CARBOTHIOAMIDES

[75] Inventors: Milton Wolf, West Chester; Richard L. Fenichel, Wyncote, both of Pa.

[73] Assignee: American Home Products Corporation, New York, N.Y.

[21] Appl. No.: 192,120

[22] Filed: Sep. 29, 1980

[51] Int. Cl.$^3$ .................. C07D 239/46; C07D 239/38; A61K 31/505
[52] U.S. Cl. .................................... 544/323; 424/251; 544/317; 544/326; 544/327; 544/329

[58] Field of Search ............... 544/317, 323, 326, 327, 544/329

[56] References Cited

FOREIGN PATENT DOCUMENTS 2354685  5/1975  Fed. Rep. of Germany ...... 544/317

Primary Examiner—Donald G. Daus
Assistant Examiner—James H. Turnipseed
Attorney, Agent, or Firm—George Tarnowski

[57] ABSTRACT

4-Amino-2-substituted-5-pyrimidinecarboxamidoximes and carbothioamides are immunomodulatory agents useful in the treatment of immune system diseases and disorders.

3 Claims, No Drawings

4-AMINO-2-SUBSTITUTED-5-PYRIMIDINECARBOXAMIDOXIMES AND CARBOTHIOAMIDES

The invention relates to novel 4-amino-2-substituted-5-pyrimidine carboxamidoximes and carbothioamides and their related derivatives, and their use as modulators of the immune response.

In recent years, the rapid upsurge in immunological research has brought about a greater appreciation and understanding of the complexities of the immune response. While the traditional overall view of the system remains, new discoveries have radically changed some thinking about the details of the system. Thus, the immune system is still divided into humoral immunity, populated with B cells and responsible for antibody formation, and cell-mediated immunity, populated with T cells and responsible for the rejection of organ transplants or skin grafts, as well as the defence mechanism against various foreign biological matter and endogenous neoplastic growths.

It is only in the last decade or so, however, that the concept has been accepted that different cell populations interact in the induction and expression of both humoral and cell-mediated immunity. Thus, subpopulations of B cells and T cells have been described, such as for example "suppressor" and "helper" T cells. In a number of animal models, it has been postulated that the helper T cells have a regulatory function in the induction of a complete antibody response by B cells to many antigens, whereas T suppressor cells are capable of preventing or terminating such responses. It is now believed that positive and negative cellular interactions control the ultimate degree of immune response. So, it is believed that any given immune response is regulated, and that the degree and mode of regulation may ultimately explain the various reactions, diseases, and disorders which are the manifestations of the operation of the organism's immune system.

The T cell subpopulations of suppressor and helper T cells have been implicated in a number of immune response manifestations. Thus, the lack or insufficiency of suppressor T cells is now believed to be a major factor in such autoimmune connective tissue disease as systemic lupus erythematosus. Moreover, in the latter case, as well as in probably impaired immune system responses such as rheumatoid arthritis, it is believed the helper T cells exacerbate the condition.

Also, the theory has been advanced that suppressor T cell hypofunctioning, resulting in inadequate T-B cell cooperation in the immune response, with continuous B cell stimulation and subsequent antibody production may be the cause of the production of antigen-antibody complexes which are the causative agents of renal and inflammatory processes in arthritis and autoimmune diseases.

Thus, it is now apparent that a number of lymphopoietic disorders are undoubtedly associated with abnormalities of T cell and especially suppressor cell function. For example, there is very strong evidence that Hodgkin's disease patients have a cellular immunity impairment, more probably, a T-lymphocyte deficiency. The loss of suppressor function is at least an early event in certain immune response diseases and is a disease-perpetuating mechanism in others. The loss of suppressor function probably leads to excessive lymphoid cell proliferation and may significantly contribute to lympho-proliferative disorders. The conditions created thereby may be exacerbated by helper T cells.

The role of immunomodulatory agents in the treatment of immune diseases and disorders, has been to suppress or stimulate the immune response, especially of cell-mediated immunity. It has been shown that enhancing or reinstituting suppressor function by immunomodulator therapy is a beneficial course of treatment for autoimmune diseases and disorders. Accordingly, immunomodulators which have a stimulatory effect on T-lymphocytes can be advantageously used in the treatment of diseases such as rheumatoid arthritis and systemic lupus erythematosus. The commercially available drug levamisole is an immunostimulant which has been used in the treatment of rheumatoid arthritis. Moreover, there is evidence to show that immunomodulators, for example immunostimulants such as levamisole, can be used as an adjunctive in the immunotherapy of metastatic diseases, such as breast cancer.

The compounds of the invention are highly active immunomodulatory agents which are especially indicated in the treatment of immune system diseases and disorders, such as systemic lupus erythematosus and rheumatoid arthritis, whose etiology is probably suppressor T cell dysfunction. The compounds of the invention are distinguished from presently known immunomodulatory agents by the fact that besides stimulating T-lymphocyte activity, the compounds also stimulate B-lymphocyte activity.

DETAILED DESCRIPTION OF THE INVENTION

The invention is directed to novel compounds having the formula:

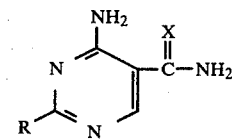

wherein X is S or NOH, and R is hydrogen, alkyl of 1–4 carbon atoms, alkylthio of 1–4 carbon atoms, amino, phenyl or phenyl substituted with fluoro, chloro, bromo, monoalkyl of 1–4 carbon atoms, dialkyl of 1–4 carbon atoms in each alkyl group, alkoxy of 1–4 carbon atoms, trifluoromethyl, carbamoyl or dialkylcarbamoyl of 1–4 carbon atoms in each alkyl moiety and pharmaceutically acceptable salts thereof.

The compounds of the invention having the general formula:

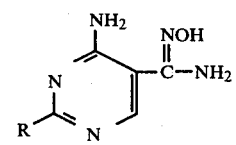

are prepared by reacting a 2-substituted-4-amino-5-pyrimidinecarbonitrile with hydroxylamine base in a dry organic solvent according to the following sequence:

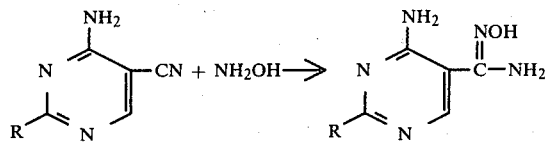

wherein R is as defined hereinbefore.

The compounds of the invention having the general formula:

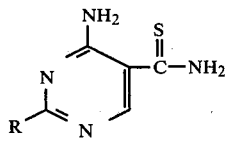

are prepared by reacting a 2-substituted-4-amino-5-pyrimidinecarbonitrile with hydrogen sulfide in the presence of pyridine and triethylamine according to the following sequence:

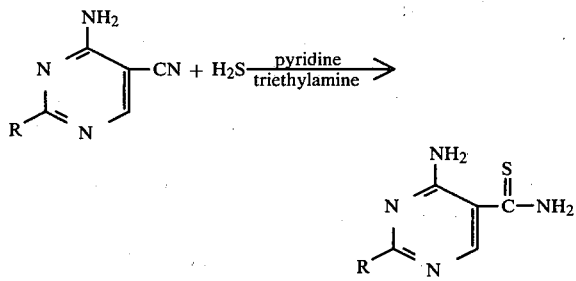

wherein R is as defined hereinbefore.

The starting material 2-substituted-4-amino-5-pyrimidinecarbonitriles can be prepared by condensing an appropriate alkyl- or aryl-amidine with an ethylenemalononitrile in alcoholic solution. If a 2-unsubstituted-4-amino-5-pyrimidinecarbonitrile is desired, formamidine is condensed with malononitrile in alcoholic solution.

The compounds of the invention are capable of forming acid addition salts, and it is intended throughout the specification and claims to embrace the pharmaceutically acceptable salts of such compounds, which salts are conveniently derived from such non-toxic inorganic and organic acids as hydrochloric, hydrobromic, nitric, sulfuric, phosphoric, methanesulfonic, p-toluenesulfonic, acetic, citric, maleic, succinic and the like.

The compounds of the invention are active immunomodulators, having activity on both the cell-mediated immune system and the humoral immune system. The compounds have therapeutic application in a variety of situations in which immunomodulation is indicated. Thus, the compounds are useful in the treatment of autoimmune diseases, such as systemic lupus erythematosus and some diseases in which a condition of immune deficiency exists, such as Hodgkins disease. Further, the compounds of the invention are also of use in the treatment of conditions such as rheumatoid arthritis.

When the compounds of the invention are employed as immunomodulators, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth methyl cellulose, sodium carboxymethyl cellulose, low melting wax, cocoa butter, and the like. Diluents, flavoring agents, solubilizers, lubricants, suspending agents, binders, tablet-disintegrating agents and the like may be employed. The compounds may be encapsulated with or without other carriers. In all cases the proportion of active ingredients in said compositions both solid and liquid will be at least sufficient to impart immunomodulatory activity thereto on oral administration. The compounds may also be injected parenterally, in which case they are used in the form of a sterile solution containing other solutes, for example, enough saline or glucose to make the solution isotonic.

The dosage requirements vary with the particular compositions employed, the route of administration, the severity of the symptoms presented and the particular subject being treated. Treatment will generally be initiated with small dosages less than the optimum dose of the compound. Thereafter, the dosage is increased until the optimum effect under the circumstances is reached. In general, the compounds of the invention are most desirably administered at a concentration level that will generally afford effective results without causing any harmful or deleterious side effects.

The immunomodulatory effect of the compounds of the invention may be demonstrated by pharmacological procedures, which are described more fully in the examples given hereinafter.

These procedures illustrate the ability of the compound of the invention to exert an immunomodulatory effect by measuring the effect of the compounds on T and B lymphocyte levels, by measuring the effect of the compounds on mitogen activated murine T lymphocyte populations, and by measuring the effect of the compounds on the inhibition or production of immunoglobulins in human lymphocyte cultures.

EXAMPLE 1

4-Amino-2-phenyl-5-pyrimidinecarboxamidoxime

A solution of hydroxylamine base is prepared by adding potassium t-butoxide (11.783 g., 0.105 m.) with stirring in a nitrogen atmosphere to a solution of hydroxylamine hydrochloride (7.296 g., 0.105 m.) in dry dimethyl sulfoxide (150 ml.) cooled to 10° C. (ice bath). After stirring at ice bath temperature for five minutes, the mixture is stirred at ambient temperature for fifteen minutes. To this is added 4-amino-2-phenyl-5-pyrimidine carbonitrile (19.621 g., 0.100 m.). The resulting solution is diluted with additional dimethyl sulfoxide (50 ml.), then heated at 40°±1° C. for seventeen hours. The dimethyl sulfoxide is distilled in vacuo (Rotovapor EL, high vacuum pump) and the residue diluted with water (250 ml.). The off-white solid is collected by filtration, washed with water, dried at 80° C./200 mm. The yield of product, m.p. 205° C. dec. (uncorr.), is 21.302 g. (95.0%). On storage, the filtrate deposits a second crop of crystals melting at 200° C. dec. (uncorrected) in a yield of 0.105 g. (0.5%). The initial product is recrystallized from ethanol-water affording colorless needles melting at 226° C. dec. (uncorr.). The yield of purified material is 63.5% (two crops).

Analysis: $C_{11}H_{11}N_5O$;

Calculated: C, 57.63; H, 4.84; N, 30.56; Found: C, 57.47, 57.36; H, 4.77, 4.69; N, 30.59, 30.61.

EXAMPLE 2

4-Amino-2-methylthio-5-pyrimidinecarboxamidoxime

A solution of hydroxylamine base, prepared from hydroxylamine hydrochloride (3.613 g., 0.050 mole) and potassium t-butoxide (5.835 g., 0.052 mole) in dry dimethyl sulfoxide (100 ml.) in a manner similar to that of Example 1, is allowed to react with 4-amino-2-methylthio-5-pyrimidine carbonitrile (8.311 g., 0.050 mole) at $40°\pm1°$ C. for 64 hours. The solvent is distilled in vacuo and the oily residue diluted with water (50 ml.) to give a pale yellow solid melting at 195° C. dec. (uncorr.) in a yield of 9.901 g. (99.4%). The initial product is recrystallized from absolute ethanol affording colorless needles melting at 210.5° C. dec. (uncorr.).

Analysis for: $C_6H_9N_5OS$; Calculated: C, 36.16; H, 4.88; N, 35.15; S, 16.09; Found: C, 36.44; H, 4.88; N, 35.50; S, 15.92.

EXAMPLE 3

2,4-Diamino-5-pyrimidinecarboxamidoxime

A solution of hydroxylamine base, prepared from hydroxylamine hydrochloride (6.949 g., 0.100 mole) and potassium t-butoxide (11.222 g., 0.100 mole) in dimethyl sulfoxide (200 ml.) in a manner similar to that of Example 1, is allowed to react with 2,4-diamino-5-pyrimidine carbonitrile (13.513 g., 0.100 mole) at $40°\pm2°$ C. for 48 hours. The insoluble solid is separated by filtration. The clear filtrate is concentrated in vacuo affording a pale yellow solid which is triturated with 2-propanol (25 ml.). The yield of crude product melting at 226° C. dec. (uncorr.) is 19.038 g. (solvated, >100%). Recrystallization of this material from water affords the title compound as colorless needles melting at 246° C. dec. (uncorr.) in a yield of 12.100 g. (72.0%).

Analysis for: $C_5H_8N_6O$;
Calculated: C, 35.71; H, 4.80; N, 49.98; Found: C, 35.44; H, 4.81; N, 49.79.

EXAMPLE 4

2,4-Diamino-5-pyrimidinecarbothioamide

Hydrogen sulfide is passed into a mixture of 2,4-diamino-5-pyrimidine carbonitrile (10.000 g., 0.0740 mole), triethylamine (10.3 ml., 0.0740 mole) and pyridine (6.0 ml., 0.074 mole) in dimethyl sulfoxide (100 ml.) for one-half hour. After storage at room temperature overnight, the brown solution is poured into water (500 ml.) with stirring. The product separates as a yellow crystalline solid which is collected by filtration, washed with water, dried at 56° C./0.1 mm. The yield of crude product melting at greater than 325° C. (uncorr.) is 12.020 g. (96.0%). Recrystallization of this material from 2-methoxyethanol affords the title compound as tan crystals melting above 350° C. (uncorr.) after drying at 110° C. at 0.1 mm.

Analysis for: $C_5H_7N_5S$; Calculated: C, 35.49; H, 4.17; N, 41.39; S, 18.94; Found: C, 35.52; H, 4.23; N, 41.20; S, 20.01.

EXAMPLE 5

4-Amino-2-methyl-5-pyrimidinecarboxamidoxime

A solution of hydroxylamine base, prepared from hydroxylamine hydrochloride (7.296 g., 0.105 mole) and potassium t-butoxide (11.783 g., 0.105 mole) in dimethyl sulfoxide (200 ml.) in a manner similar to that of Example 1, is allowed to react with 4-amino-2-methyl-5-pyrimidine carbonitrile (13.414 g., 0.100 mole). After addition of dimethyl sulfoxide (50 ml.), the mixture is heated at $40°\pm1°$ C. for 92 hours. The solid which separates is collected by filtration, successively washed with methanol (1×50 ml.) and water (3×50 ml.) then dried at 110°/0.1 mm. The yield of colorless crystals melting at 263° C. dec. (uncorr.) is 10.059 g. (60.2%). A second crop is obtained by concentrating the combined filtrates in vacuo to give a white solid. This material is washed with water, dried at 110° C./0.1 mm. The yield of colorless crystals melting at 256° C. dec. (uncorr.) is 6.300 g. (37.6%). The total yield of crude product is 16.359 g. (97.8%). The combined fractions are recrystallized from 2-methoxyethanol (Darco G-60) affording 7.887 g. (47.2%) of colorless prisms melting at 264° C. dec. (uncorr.). Concentration of the mother liquors yields a second crop of colorless prisms melting at 265° C. dec. (uncorr.) in a yield of 6.258 g. (37.4%) total yield is 14.145 g. (84.6%).

Analysis for: $C_6H_9N_5O$;
Calculated: C, 43.11; H, 5.42; N, 41.90; Found: C, 43.04; H, 5.35; N, 42.12.

EXAMPLE 6

4-Amino-5-Pyrimidinecarboxamidoxime

A. 4-Amino-5-pyrimidinecarbonitrile

Formamidine acetate (104.11 g., 1.00 mole) and malononitrile (33.03 g., 0.50 mole) are added to a solution of sodium ethoxide prepared from sodium (24.2 g., 1.05 mole) and absolute ethanol (750 ml.) in a nitrogen atmosphere. The mixture is stirred at room temperature for 48 hours. The off-white solid which separates is collected by filtration, washed with ice water then dried at 80° C./house vac. (ca. 200 mm.). The yield of product melting at greater than 340° C. (uncorr.) is 28.5 g. (47.0%). Recrystallization of this material from water (Darco G-60) affords cream-colored needles melting at 250° C. dec. (uncorr.) in a yield of 11.3 g. (18.8%).

Analysis for: $C_5H_4N_4$; Calculated: C, 49.99; H, 3.36; N, 46.65; Found: C, 49.33; 49.36; H, 3.38; 3.41; N, 46.32, 46.72.

B. 4-Amino-5-pyrimidinecarboxamidoxime

A solution of hydroxylamine base, prepared from hydroxylamine hydrochloride (6.073 g., 0.0874 mole) and potassium t-butoxide (9.808 g., 0.0874 mole) in dimethyl sulfoxide (125 ml.) in a manner similar to that of Example 1, is allowed to react with 4-amino-5-pyrimidine carbonitrile (10.000 g., 0.0832 mole) of A. above at $40°\pm1°$ C. for 30 hours. The insoluble salt is separated by filtration. The filtrate is concentrated in vacuo affording a solid. This material is washed with water then dried at 110°/0.1 mm. The yield of colorless crystals melting at 255° C. dec. (uncorr.) is 10.450 g. (82.0%). On storage at ambient temperature, the filtrate deposits a second crop melting at 208° C. dec. (uncorr.) in a yield of 0.872 g. (6.8%). The total yield crude product is 11.322 g. (88.8%). Recrystallization of the combined crops from 2-methoxyethanol, then water (Darco G-60) affords colorless needles melting at 247° C. dec. (uncorr.) in a yield of 3.950 g. (31.0%).

Analysis for: $C_5H_7N_5O$; Calculated: C, 39.21; H, 4.61; N, 45.73; Found: C, 38.70; H, 4.62; N, 45.73.

EXAMPLE 7

4-Amino-2-phenyl-5-pyrimidinecarbothioamide

Hydrogen sulfide is passed through a solution of 4-amino-2-phenyl-5-pyrimidinecarbonitrile (9.811 g., 0.050 mole) in dry pyridine (125 ml.) for one hour. The emerald green solution is stored overnight at 5° C. The solution is poured into water (500 ml.) with stirring. After stirring for one hour at ambient temperature, the pale yellow solid which separated is collected by filtration, dried at 110° C./0.1 mm. The yield of product melting at 197° C. dec. (uncorr.) was 10.481 g. (91.0%). The initial product is recrystallized from toluene (Darco G-60) affording yellow needles melting at 198° C. dec. (uncorr.) in a yield of 7.733 g. (67.1%).

Analysis for: $C_{11}H_{10}N_4S$; Calculated: C, 57.37; H, 4.37; N, 24.33; S, 13.92; Found: C, 57.43; H, 4.38; N, 24.12; S, 13.80.

EXAMPLE 8

4-Amino-2-methyl-5-pyrimidinecarbothioamide

Hydrogen sulfide is passed through a mixture of 4-amino-2-methyl-5-pyrimidinecarbonitrile (6.707 g., 0.050 m.), triethylamine (7.0 ml., 0.050 m.), dimethylformamide (25 ml.) and pyridine (100 ml.) with stirring for 3 hours at ambient temperature. The mixture is poured into ice water (500 ml.) and the cream-colored solid which separates is collected by filtration, washed with water, dried at 110° C./0.1 mm. The yield of product melting at 260° C. dec. (uncorr.) is 7.663 g. (91.1%). This material is recrystallized from dimethylformamide-water (Darco G-60) affording colorless crystals melting at 264° C. dec. (uncorr.) in a yield of 5.110 g. (60.8%).

Analysis for: $C_6H_8N_4S$; Calculated: C, 42.83; H, 4.79; N, 33.32; S, 19.06; Found: C, 42.79; H, 4.83; N, 33.34; S, 19.19.

EXAMPLE 9

4-Amino-2-methylthio-5-pyrimidinecarbothioamide

Hydrogen sulfide is passed through a suspension of 4-amino-2-methylthio-5-pyrimidinecarbonitrile (16.621 g., 0.100 mole) in a mixture of pyridine (150 ml.) and triethylamine (14.0 ml., 0.100 mole) for 2 hours. The nitrile dissolves in the course of the reaction. After ca. 1.75 hours a solid begins to separate. The mixture is poured into water (500 ml.), and the yellow solid collected by filtration washed with water, dried at 100° C., house vac. The yield of product melting at 230° C. dec. (uncorr.) is 18.93 (94.5%). This material is recrystallized from dimethylformamide-water (Darco G-60) to give yellow rods melting at 229° C. dec. (uncorr.) in a yield of 15.685 g. (78.3%).

Analysis for: $C_6H_8N_4S_2$; Calculated: C, 35.98; H, 4.02; N, 27.98; S, 32.02; Found: C, 35.86; H, 4.02; N, 28.37; S, 31.75.

EXAMPLE 10

4-Amino-2-(p-chlorophenyl)-5-pyrimidinecarboxamidoxime

A. 4-Amino-2-(p-chlorophenyl)-5-pyrimidinecarbonitrile:

Free p-chlorobenzamidine base is prepared by addition of p-chlorobenzamidine hydrochloride (30.000 g., 0.157 mole) to a solution of sodium (3.795 g., 0.165 mole) in absolute ethanol (400 ml.) in a nitrogen atmosphere. After stirring for one hour, ethoxymethylenemalononitrile (20.151 g., 0.165 mole) is added followed by ethanol (350 ml.) to facilitate stirring. After stirring at ambient temperature for ca. 70 hours, the mixture is refluxed for ten minutes, cooled, filtered and the solid product washed with ethanol (100 ml.), water (2×50 ml.) then dried at 80° C./house vac. then at 100° C./house vac./2 hours. The yield of colorless crystals melting at 267.0°–267.5° C. (uncorr.) is 27.9 g. (77.1%). The initial product is recrystallized from 1,2-dimethoxyethane affording colorless needles melting at 267.0°–267.5° C. (uncorr.) in a yield of 20.160 g. (55.7%). Concentration of the mother liquors afforded two additional crops of colorless needles: first crop (4.525 g., 12.5%), melting at 266.0°–267.5° C. (uncorr.); second crop (1.479 g., 4.1%), melting at 265.0°–265.5° C. (uncorr.).

Analysis for: $C_{11}H_7ClN_4$; Calculated: C, 57.27; H, 3.06; N, 24.29; Cl, 15.37; Found: C, 56.96; H, 3.01; N, 24.53; Cl, 15.24.

B. 4-Amino-2-(p-chlorophenyl)-5-pyrimidinecarboxamidoxime:

A solution of hydroxylamine base, prepared from hydroxylamine hydrochloride (5.76 g., 0.083 mole) and potassium t-butoxide (9.314 g., 0.083 mole) in dimethyl sulfoxide (250 ml.) in a manner similar to that of Example 1, is allowed to react with 4-amino-2-(p-chlorophenyl)-5-pyrimidinecarbonitrile (17.300 g., 0.075 mole). After addition of dimethyl sulfoxide (50 ml.) the mixture is heated at 40°±1° C. for 21 hours. The solvent is distilled in vacuo affording an off-white solid which is washed with water (3×50 ml.) then dried at 100° C./0.1 mm. The yield of crude product melting at 237.5° C. dec. (uncorr.) is 19.450 g. (98.4%). This material is recrystallized from methanol (~3.7 l)(Neutral Norit) affording almost colorless needles melting at 245° C. dec. (uncorr.) in a yield of 14.062 g. (71.1%).

Analysis for: $C_{11}H_{10}ClN_5O$; Calculated: C, 50.11; H, 3.82; N, 26.56; Found: C, 50.09; H, 3.93; N, 26.69.

EXAMPLE 11

4-Amino-2-phenyl-5-pyrimidinecarboxamidoxime is tested for its effect on the levels of circulating T and B lymphocytes in the rat according to the following procedure:

Blood is obtained by cardiac puncture (heparinized vacutainers) from fasted male rats orally dosed 18 hours before with the compound under test. The blood is centrifuged at 375 g. for 3 minutes, and the platelet rich plasma is pipetted off and discarded. The white blood cells are then separated from the other formed elements, using a gradient containing 50% hypaque with 2% methyl cellulose, and then centrifuging for 20 minutes at 1200 RPM in a Sorvall GLC-2 centrifuge.

The incubation system for rosette formation (T-lymphocytes) consists of 0.1 ml. of white cell suspension in Hanks modified balanced salt solution (HMBSS)(1.6×$10^7$ cells/ml.), 0.1 ml. of guinea pig red blood cells (6.4×$10^7$ cells/ml.) in HMBSS containing 1% bovine albumin and 0.1 ml. of HMBSS containing fetal calf serum. The tubes are incubated for 60 minutes at 37° C. and the number of rosettes per 100 white cells in the suspensions are counted under the microscope and the results expressed as the ratio of T-lymphocytes in the experimental vs. the controls.

The same white cell suspension is used for the determination of B-lymphocytes. Three to 4 drops of fluorescene conjugated rabbit-anti-rat antiserum is added to the suspension which is incubated for 1 hour at 37° C. The cell suspension is then washed twice with HMBSS and resuspended in HMBSS. The number of fluorescene stained cells in 300 white cells is counted under a fluorescence microscope, and the results expressed as the ratio of B-lymphocytes vs. the controls.

The results are summarized in Table 1.

TABLE 1

| Dose (mg/kg) | T-Lymphocytes Mean Rosettes/ 100 Cells | E/C* | B-Lymphocytes per 100 Cells | E/C* |
|---|---|---|---|---|
| 12.5 | 1.7 | 0.6 | 15 | 3 |
| 25 | 2.7 | 1.0 | 10 | 2 |
| 50 | 3.7 | 1.4 | 11 | 2.2 |
| Control | 2.7 | — | 5 | — |
| 50 | 5.0 | 3.8 | 13 | 1.9 |
| 100 | 2.0 | 1.5 | 10 | 1.4 |
| 150 | 3.0 | 2.3 | 11 | 1.6 |
| Control | 1.3 | — | 7 | — |

*E/C = Ratio of lymphocytes in the experimental group divided by lymphocytes found in the control group.

The results show that the compound tested has the capacity to increase the levels of circulating T and B lymphocytes in the rat. It is to be noted that the compound unexpectedly stimulates the activity of both T and B lymphocytes.

EXAMPLE 12

The compounds of the invention are tested to determine their effect on the proliferation of murine enriched T lymphocytes. The compounds are tested in a culture system in which T lymphocyte proliferation has been activated by the use of suboptimal concentrations of the mitogen concanavalin A (Con A) according to the following procedure:

T-lymphocytes are isolated from spleens of male CBA/J or NZB mice. Cell homogenates are prepared in Hank's balanced salt solution (HBSS). After removal of larger particles and repeated washing of the cells in HBSS, they are suspended in minimum essential medium (MEM) and passed through a glass wool column to remove macrophages. The cells are then incubated on a nylon wool column at 37° C., 95% air, 5% $CO_2$, for 45 minutes. The non-adherant T lymphocytes are then eluted from the column, counted, and adjusted to $20 \times 10^6$ cells/ml. 50 μl of cells are cultured (37° C., 95% air, 5% $CO_2$) with compound, or compound and mitogen (0.025 μg/culture of concanavalin A) for 48 hours before the addition of 0.5 μCi of $^3H$-thymidine for the last 16 hours of culture. The total volume of the culture system is 200 μl. The cells are then harvested on a multiple automatic sample harvester (Mash II), the glass fiber filter disks placed in 10 ml. of xylene base scintillation fluid, and counted for 1 minute in a liquid scintillation counter. Results are expressed as CPM±SE. Comparisons are made between counts obtained with control cultures and cultures containing compound and concanavalin A.

The results are summarized in Table 2.

The results show that compounds of the invention show a very significant T lymphocyte proliferation at very low concentrations of compound per culture, indicating that the compounds are very active immunomodulators.

TABLE 2

| Compound | Con A $^3H$ Thy cpm + S. E. | Compound concentration (μg/culture) | Compound + Con A $^3H$ Thy cpm + S. E. | p |
|---|---|---|---|---|
| 2,4-amino-5-pyrimidinecarboxamidoxime | 9859 | 0.5 | 9147 ± 1338 | |
| | | 1.0 | 15270 ± 1418 | <0.01 |
| 2-phenyl-4-amino-5-pyrimidinecarboxamidoxime | 16889 ± 1282 | 0.025 | 36155 ± 1887 | <0.05 |
| | | 0.05 | 31073 ± 2314 | <0.05 |
| 2,4-amino-5-pyrimidinecarbothioamide | 16884 ± 1282 | 0.01 | 29655 ± 2872 | <0.05 |
| | | 0.025 | 32690 ± 634 | <0.05 |
| | | 0.05 | 35307 ± 337 | <0.05 |
| 2-phenyl-4-amino-5-pyrimidinecarbothioamide | 23598 ± 1650 | 0.1 | 37122 ± 4352 | <0.05 |
| | | 1.0 | 52292 ± 2605 | <0.05 |

EXAMPLE 13

In order to determine the effect of compounds on the production or inhibition of immunoglobulins (Ig) in a human lymphocyte tube culture system, human lymphocytes are incubated for 8 days with compound and an optimal concentration of poke weed mitogen (PWM). Inhibition of Ig formation by compounds in these assay systems, in which IgG and IgM are measured, may be indicative of the capacity of the compound to limit immune complex formation through reduction of the Ig pool, and also may be indicative of augmented suppressor T cell activity.

In accordance with this procedure, an immunobead assay system is used for the detection of IgG and IgM produced in the tube cultures, in which antibody to human IgG or IgM is coupled to small hydrophilic beads. The culture sample is added to the beads and all of the Ig in the sample is bound to them, as the beads are present in excess. A fluorescein labeled monospecific antiserum is then added to the mixture, which combines with the bound antigen. After the stable complexes that are formed are separated from unreacted materials the fluoresence is measured by quantitative fluorometric techniques.

The results of the assay using 4-amino-2-phenyl-5-pyrimidinecarboxamidine are summarized in Table 3.

TABLE 3

| Compound | IgG ng/ml PWM 1:4 | IgG ng/ml PWM−CPD+PWM | IgM ng/ml PWM 1:4 | IgM ng/ml PWM−CPD+PWM |
|---|---|---|---|---|
| PWM 1:4 | 1420 | | 2310 | |
| PWM 1:4 + Lev** 1 μg | 1050 | −370 | 970 | −1340 |
| PWM 1:4 + 4-amino-2-phenyl-5-pyrimidine-carboxamidoxime 1 μg | 940 | −480 | 1130 | −1180 |
| PWM 1:4 + 4-amino-2-phenyl-5-pyrimidine-carboxamidoxime 0.1 μg | 590 | −830 | 1420 | −890 |
| PWM 1:4 + 4-amino-2- | 870 | −550 | 1360 | −950 |

TABLE 3-continued

| Compound | IgG ng/ml PWM 1:4 | IgG ng/ml PWM−CPD+PWM | IgM ng/ml PWM 1:4 | IgM ng/ml PWM−CPD+PWM |
|---|---|---|---|---|
| phenyl-5-pyrimidine-carboxamidoxime 0.01 μg | | | | |

*Compound concentrations μg/ml
**Levamisole

The results show that 4-amino-2-phenyl-5-pyrimidinecarboxamidoxime has very good inhibition of IgG and IgM at all concentration levels. This may correlate well with augmented T suppressor function.

What is claimed is:

1. A compound of the formula:

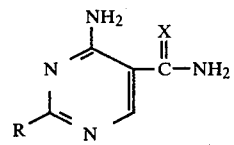

wherein X is NOH, and R is hydrogen, alkyl of 1–4 carbon atoms, alkylthio of 1–4 carbon atoms, amino, phenyl or phenyl substituted with fluoro, chloro, bromo, monoalkyl of 1–4 carbon atoms, dialkyl of 1–4 carbon atoms in each alkyl group, alkoxy of 1–4 carbon atoms, trifluoromethyl, carbamoyl or dialkylcarbamoyl of 1–4 carbon atoms in each alkyl moiety and the pharmaceutically acceptable salts thereof.

2. The compound of claim 1, which is 2,4-amino-5-pyrimidinecarboxamidoxime.

3. The compound of claim 1, which is 2-phenyl-4-amino-5-pyrimidinecarboxamidoxime.

* * * * *